US008765987B2

(12) United States Patent
Chirik et al.

(10) Patent No.: US 8,765,987 B2
(45) Date of Patent: *Jul. 1, 2014

(54) IN-SITU ACTIVATION OF METAL COMPLEXES CONTAINING TERDENTATE NITROGEN LIGANDS USED AS HYDROSILYLATION CATALYSTS

(75) Inventors: Paul J. Chirik, Princeton, NJ (US); Aaron M. Tondreau, Zurich (CH); Johannes G. P. Delis, Bergen op Zoom (NL); Kenrick M. Lewis, Flushing, NY (US); Keith J. Weller, Rensselaer, NY (US); Susan A. Nye, Feura Bush, NY (US)

(73) Assignees: Cornell University, Ithaca, NY (US); Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/302,236

(22) Filed: Nov. 22, 2011

(65) Prior Publication Data

US 2012/0130106 A1    May 24, 2012

Related U.S. Application Data

(60) Provisional application No. 61/417,084, filed on Nov. 24, 2010, provisional application No. 61/417,061, filed on Nov. 24, 2010.

(51) Int. Cl.
 *C07F 7/18* (2006.01)

(52) U.S. Cl.
 USPC ............................. 556/481; 556/467; 556/479

(58) Field of Classification Search
 USPC ........................... 556/465, 466, 467, 479, 481
 See application file for complete search history.

(56) References Cited

U.S. PATENT DOCUMENTS

| | | | |
|---|---|---|---|
| 3,159,601 | A | 12/1964 | Ashby |
| 3,220,972 | A | 11/1965 | Lamoreaux |
| 3,775,452 | A | 11/1973 | Karstedt |
| 4,729,821 | A | 3/1988 | Timmons et al. |
| 5,955,555 | A | 9/1999 | Bennett |
| 6,461,994 | B1 | 10/2002 | Gibson et al. |
| 6,657,026 | B1 | 12/2003 | Kimberley et al. |
| 7,053,020 | B2 | 5/2006 | De Boer et al. |
| 7,148,304 | B2 | 12/2006 | Kimberley et al. |
| 7,442,819 | B2 | 10/2008 | Ionkin et al. |
| 8,236,915 | B2 * | 8/2012 | Delis et al. ....................... 528/14 |
| 2011/0009565 | A1 | 1/2011 | Delis et al. |
| 2011/0009573 | A1 | 1/2011 | Delis et al. |

OTHER PUBLICATIONS

Chirik et al; Journal of American Chemical Society, 2004, 126, 13794-13807.*

Jung et al; Angewandte Chemie International Edition in English, 1996, 35, 17-42.*
Speier, John L., et al., "The Addition of Silicon Hydrides to Olefinic Double Bonds. Part II. The Use of Group VIII Metal Catalysts", Journal of the American Chemical Society, vol. 79, pp. 974-979 (1956).
Nesmeyanov, A. N. et al., "Addition, Substitution, and Telomerization Reactions of Olefins in the Presence of Metal Carbonyls or Colloidal Iron", Tetrahedron, vol. 17, pp. 61-68 (1962).
Corey, Joyce Y. et al., "Reactions of Hydrosilanes with Transition-Metal Complexes: Formation of Stable Transition-Metal Silyl Compounds", Journal of Chemical Reviews, vol. 99, pp. 175-292 (1999).
Randolph, Claudia L. et al., "Photochemical Reactions of (•5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes", Journal of The American Chemical Society, vol. 108, pp. 3366-3374 (1986).
Bart, Suzanne C. et al., "Preparation and Molecular and Electronic Structures of Iron(0) Dinitrogen and Silane Complexes and Their Application to Catalytic Hydrogenation and Hydrosilation", Journal of the American Chemical Society, vol. 126, pp. 13794-13807 (2004).
Archer, Andrew M. et al., "Arene Coordination in Bis(imino)pyridine Iron Complexes: Identification of Catalyst Deactivation Pathways in Iron-Catalyzed Hydrogenation and Hydrosilation", Organometallics, vol. 25, pp. 4269-4278 (2006).
Martinez, Remi et al., "C-C Bond Formation via C-H Bond Activation Using an in Situ-Generated Ruthenium Catalyst", Journal of the American Chemical Society, vol. 131, pp. 7887-7895 (2009).
Yi, Chae S. et al., "Regioselective Intermolecular Coupling Reaction of Arylketones and Alkenes Involving C-H Bond Activation Catalyzed by an in Situ Formed Cationic Ruthenium Hydride Complex", Organometallics, vol. 28, pp. 4266-4268 (2009).
Reiff, W. M. et al., "Mono(2,2',2"-terpyridine) Complexes of Iron(II)", Journal of Inorganic Chemistry, vol. 8, No. 9, pp. 2019-2021 (1969).
Zhang, Shu et al., "Ferrous and Cobaltous Chlorides Bearing 2,8-Bis(imino)quinolines: Highly Active Catalysts for Ethylene Polymerization at High Temperature", Organometallics, vol. 29, pp. 1168-1173 (2010).
Connelly, Neil G. et al., "Chemical Redox Agents for Organometallic Chemistry", Journal of Chemical Reviews, vol. 96, pp. 877-910 (1996).
Kroll, Roswitha et al., "Access to Heterogeneous Atom-Transfer Radical Polymerization (ATRP) Catalysts Based on Dipyridylamine and Terpyridine via Ring-Opening Metathesis Polymerization (ROMP)", Macromolecular Chemistry and Physics, vol. 202, pp. 645-653 (2001).

(Continued)

*Primary Examiner* — Sudhakar Katakam
*Assistant Examiner* — Pancham Bakshi
(74) *Attorney, Agent, or Firm* — Joseph S. Ostroff, Esq.; McDonald Hopkins LLC

(57) ABSTRACT

Disclosed herein is a process for the hydrosilylation of a composition containing a silyl hydride and a compound containing at least one unsaturated group, the process comprising contacting a non-previous metal based complex as a catalyst precursor with an activator being a reducing agent shortly before, simultaneously or after contacting the complex with the composition, to cause the silyl hydride to react with the compound containing at least one unsaturated group to produce a hydrosilylation product.

25 Claims, No Drawings

(56) References Cited

OTHER PUBLICATIONS

Glatz, Ines et al., "Terpyridine-Based Silica Supports Prepared by Ring-Opening Metathesis Polymerization for the Selective Extraction of Noble Metals", Journal of Chromatography A, vol. 1015, pp. 65-71 (2003).

Kim, Chungkyun et al, "2, 2':6',2''-Terpyridine and Bis(2,2':6',2''-terpyridine)Ruthenium(II) Complex on the Dendritic Periphery", Journal of Organometallic Chemistry, vol. 673, pp. 77-83 (2003).

Schmidt, Roland et al., "Heterogenized Iron(II) Complexes as Highly Active Ethene Polymerization Catalysts", Journal of Molecular Catalysis A: Chemical, vol. 179, pp. 155-173 (2002).

Poyatos, Macarena et al., "Coordination Chemistry of a Modular N,C-Chelating Oxazole-Carbene Ligand and Its Applications in Hydrosilylation Catalysis", Organometallics, vol. 25, pp. 2634-2641 (2006).

Castro, Pascel M. et al., "Iron-Based Catalysts Bearing Bis(imido)-Pyridine Ligands for the Polymerization of tert-Butyl Acrylate", Journal of Polymer Science: Part A: Polymer Chemistry, vol. 41, pp. 1380-1389 (2003).

Suzanne Cathleen Doucette, "Homogeneous Iron Catalysts With Redox-Active Ligands: Synthesis and Electronic Structure", Dissertation Cornell University, Aug. 2006.

* cited by examiner

IN-SITU ACTIVATION OF METAL COMPLEXES CONTAINING TERDENTATE NITROGEN LIGANDS USED AS HYDROSILYLATION CATALYSTS

CROSS-REFERENCE TO RELATED APPLICATION

This application claims priority to U.S. provisional application Nos. 61/417,084 and 61/417,061, both filed Nov. 24, 2010. The disclosures of the application Nos. 61/417,084 and 61/417,061 are herein incorporated by reference in their entireties.

FIELD OF THE INVENTION

This invention relates generally to in-situ activation of metal complexes, more specifically, to in-situ activation of tridentate metal complexes for use as hydrosilylation catalysts.

BACKGROUND OF THE INVENTION

Hydrosilylation chemistry, typically involving a reaction between a silyl hydride and an unsaturated organic group, is the basis for synthesis routes to produce commercial silicone-based products like silicone surfactants, silicone fluids and silanes as well as many addition cured products like sealants, adhesives, and silicone-based coating products. Conventionally, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's-catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal complex catalysts are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of an excess amount of allyl polyether, relative to the amount of silicone hydride, is needed to compensate for the lack of efficiency of the catalyst in order to ensure complete conversion of the silicone hydride to a useful product. When the hydrosilylation reaction is completed, this excess allyl polyether must either be: (A) removed by an additional step, which is not cost-effective, or (B) left in the product which results in reduced performance of this product in end-use applications. Additionally, the use of an excess amount of allyl polyether typically results in a significant amount of undesired side products such as olefin isomers, which in turn can lead to the formation of undesirably odoriferous by-products.

Another disadvantage of the precious metal complex catalysts is that sometimes they are not effective in catalyzing hydrosilylation reactions involving certain type of reactants. It is known that precious metal complex catalysts are susceptible to catalyst poisons such as phosphorous and amine compounds. Accordingly, for a hydrosilylation involving unsaturated amine compounds, the precious metal catalysts known in the art are normally less effective in promoting a direct reaction between these unsaturated amine compounds with silyl hydride substrates, and will often lead to the formation of mixtures of undesired isomers.

Further, due to the high price of precious metals, the precious metal-containing catalysts can constitute a significant proportion of the cost of silicone formulations. Recently, global demand for precious metals, including platinum, has increased, driving prices for platinum to record highs, creating a need for effective, low cost replacement catalysts.

As an alternative to precious metals, certain iron complexes have been disclosed as suitable for use as hydrosilylation catalysts. Illustratively, technical journal articles have disclosed that $Fe(CO)_5$ catalyzes hydrosilylation reactions at high temperatures. (Nesmeyanov, A. N. et al., Tetrahedron 1962, 17, 61), (Corey, J.Y et al., J. Chem. Rev. 1999, 99, 175), (C. Randolph, M. S. Wrighton, J. Am. Chem. Soc. 108 (1986) 3366). However, unwanted by-products such as the unsaturated silyl olefins, which are resulted from dehydrogenative silylation, were formed as well.

A five-coordinate Fe (II) complex containing a pyridine di-imine (PDI) ligand with isopropyl substitution at the ortho positions of the aniline rings has been used to hydrosilate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective with the aforementioned primary and secondary phenyl-substituted silanes, and not with, for example, tertiary or alkyl-substituted silanes such as $Et_3SiH$, or with alkoxy substituted silanes such as $(EtO)_3SiH$.

Other Fe-PDI complexes have also been disclosed. U.S. Pat. No. 5,955,555 discloses the synthesis of certain iron or cobalt PDI dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. However, the catalysts and catalyst systems disclosed in these references are described for use in the context of olefin polymerizations and/or oligomerisations, not in the context of hydrosilylation reactions.

Recently new and inexpensive Fe, Ni, Co and Mn complexes containing a terdentate nitrogen ligand have been found to selectively catalyze hydrosilylation reactions, as described in U.S. Patent Application Publication Nos. 20110009573 and 20110009565, the contents of which are incorporated herein by reference in their entirety. In addition to their low cost and high selectivity, the advantage of these catalysts is that they can catalyze hydrosilylation reactions at room temperature while precious metal based catalysts typically work only at elevated temperatures.

A restriction of these new non-precious metal-based catalysts, however, is that they are normally air and moisture sensitive, thus may not perform well if exposed to air or moisture prior to their use. For this reason, these catalysts are typically prepared and stored under inert conditions. Since it is difficult to keep reaction mixtures under inert conditions, such as a nitrogen blanket, on a commercial scale, the manufacturing of these catalysts in an industrial setting may be economically prohibitive. Accordingly, there is a need in the industry for non-precious metal-based catalysts that do not require manufacturing and storing under inert conditions.

Methods are known in the art to activate catalyst precursors in-situ. The most well known example is the activation of Ziegler-Natta catalyst by Methylaluminoxane (MAO) for the production of polypropylene from propene (Y. V. Kissin Alkene Polymerization Reactions with Transition Metal Catalysts, Elsevier, 2008, Chapter 4).

U.S. Pat. No. 5,955,555 discloses the activation of certain iron or cobalt PDI dianion complexes by polymethylaluminoxane (PMAO) for olefin polymerization. U.S. Pat. No. 4,729,821 discloses the in-situ activation of Ni-catalysts by applied electrical potentials for the hydrogenolysis of ethane and ethylene.

Martinez et al. demonstrated the in-situ activation of a [RuCl$_2$(p-cym)]$_2$ complex by phosphine ligands in a C—C bond formation reaction via C—H bond activation of aryl-compounds (J. Am. Chem. Soc, 2009, 131, 7887).

Yi et al. described the in-situ formation of cationic Ruthenium hydride complexes which catalyze the regioselective intermolecular coupling reaction of Arylketones and Alkenes involving C—H bond activation (Organometallics, 2009, 28, 426).

However, the in-situ activation of non-precious metal-based catalysts for hydrosilation reactions has not been known to the knowledge of the present inventors. Accordingly, there is a continuing need in the hydrosilylation industry for such methods. The present invention provides an answer to that need.

SUMMARY OF THE INVENTION

In one aspect, the present invention is directed to a process for the hydrosilylation of a reaction mixture containing a silyl hydride and a compound containing at least one unsaturated group. The process includes the steps of:
  (i) providing a catalyst precursor being a complex having a structural formula according to Formula (I), Formula (II), or Formula (III);
  (ii) activating the catalyst precursor by contacting the catalyst precursor with an activator in the presence of a liquid medium containing at least one component selected from the group consisting of a solvent, the silyl hydride, the compound containing at least one unsaturated group, and combinations thereof, thereby providing an activated catalyst;
  (iii) reacting the silyl hydride and the compound containing at least one unsaturated group in the presence of the activated catalyst to produce a hydrosilylation product containing the activated catalyst or derivatives thereof, wherein step (ii) is conducted shortly before, or at the same time as, step (iii); and
  (iv) optionally removing the activated catalyst or derivatives thereof,
wherein Formula (I), Formula (II) and Formula (III) are:

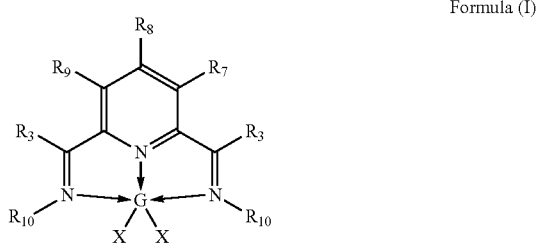

Formula (I)

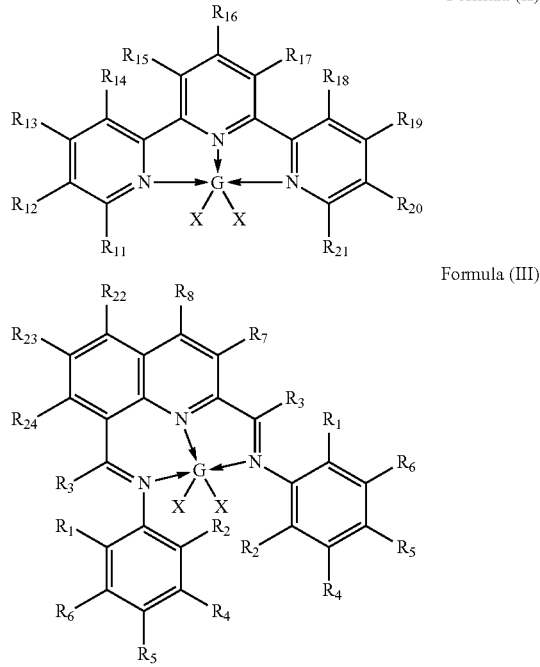

Formula (II)

Formula (III)

wherein
  G is Mn, Fe, Ni, or Co;
  each occurrence of $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ is independently H, C1-18 alkyl, C1-C18 substituted alkyl, aryl, substituted aryl, or an inert group, wherein any two of $R_1$-$R_3$, $R_3$-$R_7$, $R_3$-$R_9$, $R_{14}$-$R_{15}$ and $R_{17}$-$R_{18}$ vicinal to one another taken together may form a ring being a substituted or unsubstituted, saturated, or unsaturated cyclic structure, wherein $R_2$ to $R_9$, and $R_{11}$ to $R_{24}$ other than hydrogen, optionally contain at least one heteroatom;
  each occurrence of $R_{10}$ is independently C1-C18 alkyl group, C1-C18 substituted alkyl, aryl or substituted aryl group, wherein $R_{10}$ optionally contains at least one heteroatom; and
  X is an anion.

In another aspect, the present invention is directed to a process for selectively producing a mono-hydrosilylated product from a reaction mixture containing a silyl hydride and a polyunsaturated compound. The process includes the steps of:
  (i) providing a catalyst precursor being a complex having a structural formula according to Formula (I), Formula (II), or Formula (III) as described above;
  (ii) activating the catalyst precursor by contacting the catalyst precursor with an activator in the presence of a liquid medium containing at least one component selected from the group consisting of a solvent, the silyl hydride, the polyunsaturated compound, and combinations thereof, thereby providing an activated catalyst;
  (iii) reacting the silyl hydride and the polyunsaturated compound in the presence of the activated catalyst such that hydrosilylation occurs selectively at one unsaturated group of the polyunsaturated compound, thereby producing the mono-hydrosilylated product containing the activated catalyst or derivatives thereof, wherein step (ii) is conducted shortly before, or at the same time as, step (iii); and (iv) optionally removing the activated catalyst or derivatives thereof, wherein the polyunsaturated compound is represented by Formula (X) or Formula (XI)

$$E^1[(CH_2)_\beta CR^1{=}CH_2]_\alpha, \quad \text{(Formula X)}$$

$$R^2_\gamma E^2[(CH_2)_\beta CR^1{=}CH_2]_\alpha, \quad \text{(Formula XI)}$$

wherein $E^1$ is a divalent or polyvalent aliphatic or aromatic cyclic hydrocarbon group containing from 3 to 25 carbon atoms, or a divalent or polyvalent aliphatic or aromatic heterocyclic hydrocarbon containing from 3 to 25 carbon atoms, wherein the heteroatom is selected from the group consisting of oxygen, nitrogen, silicon and sulfur;

$E^2$ is a divalent or polyvalent cyclic silicone group containing from 3 to 8 silicon atoms and from 3 to 8 oxygen atoms;

each occurrence of $R^1$ and $R^2$ is independently a hydrogen or a hydrocarbon group containing from 1 to 8 carbon atoms;

each occurrence of $\alpha$, $\beta$ and $\gamma$ is independently an integer, wherein $\alpha$ is 2 to 6; $\beta$ is 0 to 6; and $\gamma$ is 0 to 4; and wherein the molar ratio of the Si—H functional groups in the silyl hydride to the alkenyl functional groups in the unsaturated compound is between about $(0.5/\alpha)$ and about $(1.1/\alpha)$.

In yet another aspect, the present invention is directed to a composition produced from the above described selectively mono-hydrosilylation process, wherein the composition contains a mono-hydrosilylated product and a bis-hydrosilylated product; wherein the gravimetric ratio of the mono-hydrosilylated product to the bis-hydrosilylated product is greater than about 1.8, and wherein the composition contains the complex of Formula (I), (II) or (III) or derivatives thereof.

These and other aspects will become apparent upon reading the following description of the invention.

DETAILED DESCRIPTION OF THE INVENTION

It has now been surprisingly found that five-coordinate non-precious metal based complexes containing a terpyridine, a pyridinediimine or a quinoline based terdentate nitrogen ligand can be activated in-situ by a reducing agent to generate effective catalysts for the hydrosilylation of a silyl hydride and an unsaturated hydrocarbon.

As used herein, it is appreciated that "in-situ" means that (1) the catalyst precursor is activated while the catalyst precursor is present in the reaction mixture of the silyl hydride and the unsaturated substrate, or (2) the catalyst precursor is partially or fully activated before the partially or fully activated catalyst is present in the reaction mixture of the silyl hydride and the unsaturated substrate. It is intended to include the following situations: (a) contacting the catalyst precursor with an activator in the presence of a solvent to provide an admixture shortly before contacting the admixture with the silyl hydride and the unsaturated substrate, or (b) contacting the catalyst precursor with an activator in the presence of the silyl hydride to provide an admixture shortly before contacting the admixture with the unsaturated substrate, and if necessary, the remaining amount of the silyl hydride, or (c) contacting the catalyst precursor with an activator in the presence of the unsaturated substrate to provide an admixture shortly before contacting the admixture with the silyl hydride, and if necessary, the remaining amount of the unsaturated substrate, or (d) contacting the catalyst precursor with an activator at the same time as, or after, contacting the catalyst precursor with the silyl hydride and the unsaturated substrate.

By "shortly before", it is meant a time period of less than 24 hours, specifically less than 2 hours, more specifically, less than 30 minutes depending upon the properties of the particular catalyst precursor and the activator used.

The catalyst precursor, namely, a complex of the Formula (I), (II) or (III) has been described above. In connection with these formulae, G can be Mn, Fe, Ni, or Co in all the valence state. Advantageously G is iron or cobalt. More advantageously, M is Fe, such as Fe (II) and Fe (III).

X can be $F^-$, $Cl^-$, $Br^-$, $I^-$, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group. Preferably, X is $F^-$, $Cl^-$, $Br^-$, $I^-$, more preferably $Cl^-$ or $Br^-$.

Each occurrence of $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ is independently H, C1-18 alkyl, specifically C1-C10 alkyl, more specifically C1-C6 alkyl, C1-C18 substituted alkyl, preferably C1-C10 substituted alkyl, more preferably C1-C6 substituted alkyl, aryl, substituted aryl, or an inert group. In some embodiments, any two of $R_1$-$R_3$, $R_3$-$R_7$, $R_3$-$R_9$, $R_{14}$-$R_{15}$ and $R_{17}$-$R_{18}$ vicinal to one another taken together form a ring being a substituted or unsubstituted, saturated, or unsaturated cyclic structure. $R_2$ to $R_9$, and $R_{11}$ to $R_{24}$ other than hydrogen may optionally contain at least one heteroatom, for example, an oxygen atom, a silicon atom, or a halide.

Each occurrence of $R_{10}$ is independently C1-C18 alkyl, specifically C1-C10 alkyl, more specifically C1-C6 alkyl, C1-C18 substituted alkyl, specifically C1-C10 substituted alkyl, more specifically C1-C6 substituted alkyl, aryl or substituted aryl group, wherein $R_{10}$ optionally contains at least one heteroatom.

As used herein, "alkyl" includes straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially interfere with the hydrosilylation processes described herein. In one embodiment, the substituent group is an inert functional group described herein.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl, and naphthalenyl.

By "substituted aryl" herein is meant an aromatic group that contains one or more substituent groups that are inert under the process conditions to which the compound containing these substituent groups is subject. The substituent groups also do not substantially interfere with the hydrosilylation processes described herein. Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, the substituents of the substituted aryl groups herein contain 0 to about 30 carbon atoms, specifically from 0 to 20 carbon atoms, more specifically from 0 to 10 carbon atoms. In one embodiment, the substituent group is an inert functional group described herein.

By "inert functional group" herein is meant a group other than hydrocarbyl or substituted hydrocarbyl which is inert under the process conditions to which the compound containing the group is subjected. The inert functional groups also do not substantially interfere with any hydrosilylation process described herein. Examples of inert functional groups include halo (fluoro, chloro, bromo, and iodo), ether such as —$OR^{30}$ wherein $R^{30}$ is hydrocarbyl or substituted hydrocarbyl.

"Heteroatom" herein is meant any of the Group 13-17 elements except carbon, and can include for example oxygen, nitrogen, silicon, sulfur, phosphorus, fluorine, chlorine, bromine, and iodine.

In some embodiments, the catalyst precursors disclosed herein include those of Formula (I) having the following substituents: (1) at least one of $R_{10}$ is

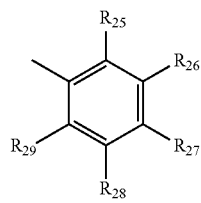

Formula (XXI)

wherein each occurrence of $R_{25}$, $R_{26}$, $R_{27}$, $R_{28}$ and $R_{29}$ is independently hydrogen, C1-C18 alkyl, C1-C18 substituted alkyl, aryl, substituted aryl or an inert functional group, wherein $R_{25}$ to $R_{29}$, other than hydrogen, optionally contain at least one heteroatom; and/or (2) at least one of $R_{10}$ is a C1-C6 alkyl, and/or (3) $R_3$ is methyl; and/or (4) $R_7$-$R_9$ are hydrogen.

In connection with Formula (XXI), advantageously, $R_{27}$ is hydrogen, methyl, ethyl, n-propyl or isopropyl group; and/or $R_{25}$ and $R_{29}$ are both methyl, ethyl, n-propyl or isopropyl groups; and/or $R_{26}$ and $R_{28}$ are hydrogen.

In connection with Formula (II), in some embodiments, $R_{16}$ is aryl or substituted aryl, and/or $R_{11}$ to $R_{15}$, $R_{17}$ to $R_{21}$ are hydrogen. In other embodiments, $R_{11}$ to $R_{21}$ are hydrogen.

In some embodiments, the catalyst precursors of Formula (III) having the following substituents: (1) $R_1$ to $R_3$ are methyl, $R_4$ to $R_8$ are hydrogen, and $R_{22}$ to $R_{24}$ are hydrogen; or (2) $R_1$ and $R_3$ are methyl, $R_2$ is hydrogen, $R_4$ to $R_8$ are hydrogen, and $R_{22}$ to $R_{24}$ are hydrogen; or (3) $R_1$ to $R_3$, and $R_5$ are methyl, $R_4$ is hydrogen, $R_6$ to $R_8$ are hydrogen, and $R_{22}$ to $R_{24}$ are hydrogen.

The methods to prepare the catalyst precursors of the present invention are known to a person skilled in the field. The complex of Formula (I) can be prepared by reacting a PDI ligand with a metal halide, such as $FeBr_2$. Typically, the PDI ligands are produced through condensation of an appropriate amine or aniline with 2,6-diacetylpyridine and its derivatives. If desired, the PDI ligands can be further modified by known aromatic substitution chemistry. An exemplary method to prepare the complex of Formula (II) can be found at *Inorganic Chemistry* (1969), 8(9), 2019-2021 to Reiff et al., which is incorporated herein by reference in its entirety. An exemplary method to prepare the complex of Formula (III) can be found at *Organometallics* (2010), 29(5), 1168-1173 to Zhang et al., the disclosure of which is incorporated herein by reference in its entirety.

The metal complexes of Formulae (I), (II) and (III) can be activated in-situ to generate reactive catalysts effective to selectively catalyzing industrially practiced hydrosilylation reactions. For example, these catalyst precursors can be used in the reactions involving: (1) the crosslinking of silicone hydride fluids with terminally unsaturated polymers, and (2) hydrosilylation of terminally unsaturated amines with tertiary silanes. Accordingly, the catalyst precursors of the invention have utility in the preparation of useful silicone products, including, but not limited to, coatings such as release coatings, room temperature vulcanizates, sealants, adhesives, products for agricultural and personal care applications, and silicone surfactants for stabilizing polyurethane foams.

The activators suitable for the present invention include reducing agents having a reduction potential more negative than −0.6 v versus ferrocene in the presence of nitrogen, as described in *Chem. Rev.* 1996, 96, 877-910. In one embodiment, the reducing agents have a reduction potential in the range of −2.8 to −3.1 v versus ferrocene. Exemplary reducing agents include, but are not limited to, sodium naphthalenide, Mg(butadiene).2THF, Mg(Anthracenide).3THF, $NaEt_3BH$, $LiEt_3BH$, diisobutylaluminum hydride, and combinations thereof.

When used as catalyst precursors for the hydrosilylation reaction, the complexes of Formulae (I), (II) and (III) can be supported or immobilized on a support material, for example, carbon, silica, alumina, $MgCl_2$ or zirconia, or on a polymer or prepolymer, for example polyethylene, polypropylene, polystyrene, or poly(aminostyrene). The metal complexes can also be supported on dendrimers.

In some embodiments, for the purposes of attaching the catalyst precursors of the invention to a support, it is desirable that at least one of $R_1$ to $R_9$ or $R_{11}$ to $R_{24}$ of the metal complexes having structural Formulae (I), (II) and (III), has a functional group that is effective to covalently bond to the support. Exemplary functional groups include but are not limited to SH, COOH, $NH_2$ or OH groups.

In certain embodiments, silica supported catalyst precursors may be prepared via Ring-Opening Metathesis Polymerization (ROMP) technology as discussed in the literature, for example Macromol. Chem. Phys. 2001, 202, No. 5, pages 645-653; Journal of Chromatography A, 1025 (2003) 65-71, the disclosure of which is incorporated herein by reference in its entirety.

In some embodiments, the catalyst precursors can be immobilized on the surface of dendrimers by the reaction of Si—Cl bonded parent dendrimers and functionalized complexes of Formulae (I), (II) and (III) in the presence of a base is as illustrated by Kim et al. in Journal of Organometallic Chemistry 673 (2003) 77-83, the disclosure of which is incorporated herein by reference in its entirety.

The catalyst precursors of the invention, either supported or unsupported, can be activated in-situ to generate reactive catalysts for the hydrosilylation of a composition containing a silyl hydride and a compound having at least one unsaturated group. The process includes the steps of: (i) providing a complex according to Formula (I), Formula (II) or Formula (III), (ii) contacting the complex with an activator, optionally in the presence of a solvent, shortly before, simultaneously, or after contacting the complex with the composition, to cause the silyl hydride to react with the compound containing at least one unsaturated group to produce a hydrosilylation product containing said complex and/or complex derivatives, and (iii) optionally removing the complex and/or complex derivatives from the hydrosilylation product.

As used herein, by "unsaturated" is meant one or more double or triple bonds. In a preferred embodiment, it refers to carbon-carbon double or triple bonds.

The temperature range for the process of the hydrosilylation is from −50° C. to 250° C., advantageously from −10 to 150° C. The silyl hydride and the compound having at least one unsaturated group are typically mixed in a molar ratio ranging from about 0.5:2 to about 1:0.8, advantageously from about 0.8:1.3 to about 1:0.9, and more advantageously in a molar ratio of 1:1 of the reactive groups. The molar ratio of the reducing agent or the activator with respect to the catalyst precursor is between about 5:1 and 0.8:1, advantageously between about 2:1 and 0.8:1, more advantageously between about 1.2:1 to about 0.8:1. The amount of catalyst in the reaction mixture calculated on ppm level of the metal in the total mass of the mixture is 1-10,000 ppm, advantageously 10-5000 ppm, more advantageously 20-2000 ppm. For an in-situ activation, a nitrogen atmosphere is preferred, but is not absolutely necessary.

The silyl hydride employed in the hydrosilylation reaction is not particularly limited. It can be any compound selected from the group consisting of $R_aSiH_{4-a}$, $(RO)_aSiH_{4-a}$, $HSiR_a(OR)_{3-a}$, $Q_uT_vT_p^HD_wD^H_xM^H_yM_z$, $R_3Si(CH_2)_f(SiR_2O)_eSiR_2H$, $(RO)_3Si(CH_2)_f(SiR_2O)_eSiR_2H$ and combinations thereof. The silyl hydride can contain linear, branched or cyclic structures, or combinations thereof. As used herein, each occurrence of R is independently C1-C18 alkyl, specifically C1-C10 alkyl, more specifically C1-C6 alkyl, C1-C18 substituted alkyl, specifically C1-C10 substituted alkyl, more specifically C1-C6 substituted alkyl, aryl, and substituted aryl, wherein R optionally contains at least one heteroatom, each occurrence of a independently has a value from 1 to 3, f has a value of 1 to 8, e has a value of 1 to 11, each of p, u, v, y and z independently has a value from 0 to 20, w and x are from 0 to 1000, provided that p+x+y equals 1 to 3000 and the valences of the all the elements in the silyl hydride are satisfied. Preferably, f is from 2 to 4, e is from 1-3, p, u, v, y, and z are from 0 to 10, w and x are from 0 to 100, wherein p+x+y equals 1 to 100.

As used herein, an "M" group represents a monofunctional group of formula $R'_3SiO_{1/2}$, a "D" group represents a difunctional group of formula $R'_2SiO_{2/2}$, a "T" group represents a trifunctional group of formula $R'SiO_{3/2}$, and a "Q" group represents a tetrafunctional group of formula $SiO_{4/2}$, an "$M^H$" group represents $H_gR'_{3-g}SiO_{1/2}$, a "$T^H$" represents $HSiO_{3/2}$, and a "$D^H$" group represents $R'HSiO_{2/2}$. As used herein, g is an integer from 0 to 3. Each occurrence of R' is independently C1-C18 alkyl, specifically C1-C10 alkyl, more specifically C1-C6 alkyl, C1-C18 substituted alkyl, specifically C1-C10 substituted alkyl, more specifically C1-C6 substituted alkyl, aryl, and substituted aryl, wherein R' optionally contains at least one heteroatom.

In some embodiments, the silyl hydride has a structure of

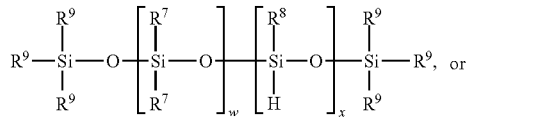

(Formula VII)

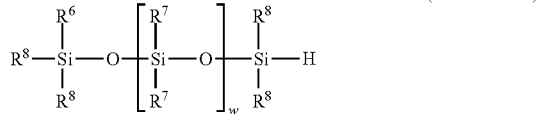

(Formula VIII)

wherein each occurrence of $R^7$, $R^8$ and $R^9$ is independently a C1-C18 alkyl, C1-C18 substituted alkyl, aryl, or a substituted aryl, $R^6$ is hydrogen, a C1-C18 alkyl, C1-C18 substituted alkyl, aryl, or a substituted aryl, and w and x are independently greater than or equal to 0.

The compound containing an unsaturated group employed in the hydrosilylation reaction includes, but is not limited to, unsaturated polyethers such as alkyl-capped allyl polyethers, vinyl functionalized alkyl capped allyl or methallyl polyether; terminally unsaturated amines such as allyl amine, N,N-dimethylallylamine; alkynes; C2-C18 olefins, preferably alpha olefins such as 1-octene; unsaturated cycloalkyl epoxides including limonene oxides, and vinyl cyclohexyl epoxides such as 4-vinyl-1-cyclohexene 1,2-epoxide; unsaturated alkyl epoxide include 1,2-epoxy-7-octene, 1,2-epoxy-9-decene, butadiene monoxide, 2-methyl-2-vinyloxirane, 1,2-epoxy-5-hexene, and allyl glycidyl ether; terminally unsaturated acrylates or methyl acrylates; unsaturated aryl ethers; unsaturated aromatic hydrocarbons such as styrene; unsaturated cycloalkanes such as trivinyl cyclohexane; vinyl-functionalized polymer such as terminally unsaturated polyurethane polymers; and vinyl-functionalized silanes and vinyl-functionalized silicones.

Unsaturated polyethers suitable for the hydrosilylation reaction preferably are polyoxyalkylenes having the general formula:

(Formula IV) or

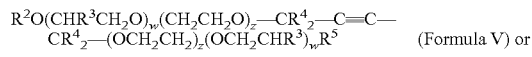

(Formula V) or

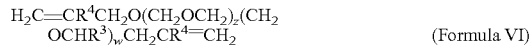

(Formula VI)

wherein $R^1$ denotes an unsaturated organic group containing from 2 to 10 carbon atoms such as allyl, methallyl, propargyl or 3-pentynyl. When the unsaturation is olefinic, it is desirably terminal to facilitate smooth hydrosilylation. However, when the unsaturation is a triple bond, it may be internal. $R^2$ is vinyl, or a polyether capping group of from 1 to 8 carbon atoms such as the alkyl groups: $CH_3$, $n-C_4H_9$, $t-C_4H_9$ or $i-C_8H_{17}$, the acyl groups such as $CH_3COO$, $t-C_4H_9COO$, the beta-ketoester group such as $CH_3C(O)CH_2C(O)O$, or a trialkylsilyl group. $R^3$ and $R^4$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^4$ may also be hydrogen. Methyl is the most preferred $R^3$ and $R^4$ groups. $R^5$ is vinyl, or a polyether capping group of from 1 to 8 carbon atoms as defined herein above for $R^2$. Each occurrence of z is 0 to 100 inclusive and each occurrence of w is 0 to 100 inclusive. Preferred values of z and w are 1 to 50 inclusive.

Vinyl functionalized silicones are $Q_uT_vT_p^{vi}D_wD^{vi}_xM^{vi}_yM_z$, wherein Q is $SiO_{4/2}$, T is $R'SiO_{3/2}$, $T^{vi}$ is $R^{12}SiO_{3/2}$, D is $R'_2SiO_{2/2}$, $D^{vi}$ is $R'R^{12}SiO_{2/2}$, $M^{vi}$ is $R^{12}_gR'_{3-g}SiO_{1/2}$, M is $R'_3SiO_{1/2}$; $R^{12}$ is vinyl; each occurrence of R' is independently C1-C18 alkyl, C1-C18 substituted alkyl, aryl, substituted aryl, wherein R' optionally contains at least one heteroatom; each g has a value of from 1 to 3, p is from 0 to 20, u is from 0 to 20, v is from 0 to 20, w is from 0 to 5000, x is from 0 to 5000, y is from 0 to 20, and z is from 0 to 20, provided that v+p+w+x+y equals 1 to 10,000, and the valences of all of the elements in the compound containing at least one unsaturated group are satisfied.

In some embodiments, suitable vinyl functionalized silicones are represented by Formula (IX):

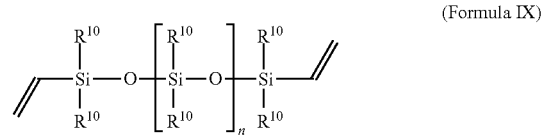

(Formula IX)

wherein each occurrence of $R^{10}$ is independently a C1-C18 alkyl, C1-C18 substituted alkyl, vinyl, aryl, or a substituted aryl, n is greater than or equal to zero.

Vinyl functional silanes are $R^{14}{}_aSiR^{15}{}_{4-a}$, wherein $R^{14}$ is C1-C18 alkyl, C1-C18 substituted alkyl, aryl, substituted aryl, wherein $R^{14}$ optionally contains at least one heteroatom, and $R^{15}$ is vinyl and wherein a has a value from 0 to 3.

The metal complexes of the invention can also be used in a process for preparing a silylated polyurethane, which includes the step of contacting a terminally unsaturated polyurethane polymer with a silyl hydride in the presence of a catalyst generated in-situ from a catalyst precursor of Formula (I), (II), or (III).

After being activated by the activator, the complexes of Formula (I), (II), and (III) are efficient and selective in catalyzing hydrosilylation reactions. For example, when the metal complexes of the invention are employed in the hydrosilylation of an alkyl-capped allyl polyether and a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is unsaturated amine compound, the hydrosilylation product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

Accordingly, in some embodiments, the present invention is also directed to the compositions produced from the above described methods. These compositions contain the hydrosilylated products of the silyl hydride and the compound having at least one unsaturated group plus the complex of Formula (I), (II) or (III) or derivatives thereof. In some embodiments, the compositions also contain derivatives from the reducing agents.

After being activated in-situ by an activator, the catalyst precursors of Formula (I), (II) or (III) are effective for mono-hydrosilylation of a polyunsaturated compound. Accordingly, in one embodiment, the present invention is directed to a process for the selective mono-hydrosilylation of a composition containing a silyl hydride and a polyunsaturated compound. The process includes steps of (i) providing a catalyst precursor being a complex having a structural formula according to Formula (I), Formula (II) or Formula (III) as described above, optionally in the presence of a solvent; (ii) activating the catalyst precursor by contacting the catalyst precursor with an activator in the presence of a liquid medium containing at least one component selected from the group consisting of a solvent, the silyl hydride, the polyunsaturated compound, and combinations thereof, thereby providing an activated catalyst; (iii) reacting the silyl hydride and the polyunsaturated compound in the presence of the activated catalyst such that hydrosilylation occurs selectively at one unsaturated group of the polyunsaturated compound, thereby producing the mono-hydrosilylated product containing the activated catalyst or derivatives thereof, wherein step (ii) is conducted shortly before, or at the same time as, step (iii); and (iv) optionally removing the activated catalyst or derivatives thereof. The mono-hydrosilylation product can be subsequently recovered from the reaction mixture, for example, by distillation.

The polyunsaturated compound is represented by Formula (X) or Formula (XI)

$$E^1[(CH_2)_\beta CR^1=CH_2]_\alpha,\quad\text{(Formula X)}$$

$$R^2{}_\gamma E^2[(CH_2)_\beta CR^1=CH_2]_\alpha,\quad\text{(Formula XI)}$$

In connection with Formula (X), $E^1$ is a divalent or polyvalent aliphatic or aromatic cyclic hydrocarbon group containing from 3 to 25 carbon atoms, or a divalent or polyvalent aliphatic or aromatic heterocyclic hydrocarbon group containing from 3 to 25 carbon atoms. Suitable heteroatom includes, but is not limited to oxygen, nitrogen, silicon and sulfur. In one embodiment, $E^1$ contains from 4 to 20 carbon atoms. In another embodiment, $E^1$ contains from 4 to 15 carbon atoms. Exemplary $E^1$ includes aliphatic cyclic hydrocarbons such as cyclohexyl; aromatic cyclic hydrocarbons such as benzene ring; heterocyclic moiety such as a cyanurate, isocyanurate, or triazine ring. Advantageously, $E^1$ is cyclohexyl or a benzene ring.

In connection with Formula (XI), $E^2$ is a divalent or polyvalent cyclic silicone group containing from 3 to 8 silicon atoms and from 3 to 8 oxygen atoms. Exemplary $E^2$ includes cyclotrisiloxane and cyclotetrasiloxane rings.

In connection with Formula (X) and Formula (XI), each occurrence of $R^1$ and $R^2$ is independently hydrogen or a hydrocarbon group containing from 1 to 8 carbon atoms. In one embodiment, $R^1$ is hydrogen or a C1-C4 alkyl group. In another embodiment, $R^2$ is hydrogen, a methyl or ethyl group.

Each occurrence of $\alpha$, $\beta$ and $\gamma$ is independently an integer. $\alpha$ has a value of from 2 to 6, preferably from 3 to 6; $\beta$ has a value from zero to 6, advantageously from zero to 2; and $\gamma$ has a value of from 0 to 4.

Advantageously, the polyunsaturated compound is a polyalkenyl compound. Examples of the polyalkenyl compounds are the trivinylcyclohexanes, trivinylbenzenes, tetravinylcyclobutane, trivinyltrimethylcyclotrisiloxane, tetramethyltetravinylcyclotetrasiloxane, triallylcyanurate, and triallylisocyanurate. Trivinylcyclohexanes are preferred.

The silyl hydride employed in the hydrosilylation reaction is not particularly limited and have been described above. In some embodiments, the silyl hydride has one of the following structures:

$$R^3{}_a(R^4O)_b SiH \quad\text{(Formula XV)}$$

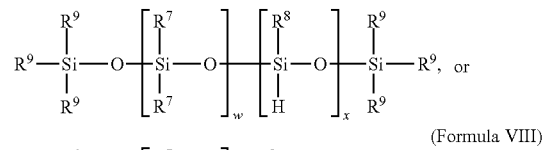
(Formula VII)

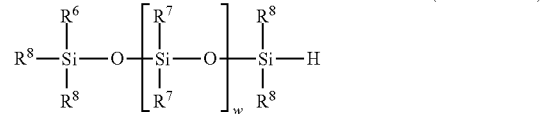
(Formula VIII)

wherein each occurrence of $R^3$, $R^4$, $R^7$, $R^8$, and $R^9$ is independently a C1-C18 alkyl, C1-C18 substituted alkyl, aryl, or substituted aryl, $R^6$ is hydrogen, a C1-C18 alkyl, C1-C18 substituted alkyl, aryl, or substituted aryl, w and x are independently greater than or equal to 0, a and b are integers 0 to 3, with the proviso that a+b=3.

Exemplary silyl hydrides suitable for the selectively mono-hydrosilylation process of present invention include, but are not limited to, trialkylsilanes like $(C_2H_5)_3SiH$, trialkoxysilanes like $(CH_3O)_3SiH$ and $(C_2H_5O)_3SiH$, hydridodisiloxanes like $(CH_3)_3SiOSi(CH_3)_2H$, hydridotrisiloxanes like

[(CH₃)₃SiO]₂SiH(CH₃), and hydridocyclosiloxanes like [(CH₃)₂SiO]₃OSiH(CH₃) and [(CH₃)₂SiO]₄OSiH(CH₃).

In the composition to be reacted for the formation of the mono-hydrosilylated product, the molar ratio of Si—H functional groups in the silyl hydride to the alkenyl functional groups in the polyunsaturated compound is between about (0.5/α) and about (1.1/α), where α is an integer from 2 to 6. If the ratio is lower than about (0.5/α), the reaction would end up with large quantities of unreacted polyunsaturated compound. If the ratio is greater than about (1.1/α), the reaction would produce excessive bis-hydrosilylation products, thus resulting in reduced selectivity. Advantageously, the ratio is about (1/α). Selective mono-hydrosilylation is favored by slow addition of the silyl hydride to the reaction mixture comprising the polyunsaturated compound and the non-precious metal-based catalyst precursor as described above.

The amount of catalyst precursor in the reaction mixture calculated based on the non-precious metal catalyst precursor in the total mass of the reaction mixture is 1-10,000 parts per million (ppm), specifically 10-5000 ppm, more specifically 20-2000 ppm.

The temperature of the reaction leading to selective mono-hydrosilylation can be from about −50° C. to about 120° C., specifically from 0° C. to 80° C. and, more specifically, from 10° C. to 60° C. Since the hydrosilylation is exothermic, it might be necessary to apply cooling to control the temperature with narrow limits, depending on the particular polyunsaturated compound and silyl hydride used.

Solvents aid in the dissolution of the catalysts as well as in the control of reaction rate. Hydrocarbon solvents such as toluene and pentane are suitable. Selective mono-hydrosilylation is favored by dissolving the silyl hydride in the solvent and adding the solution slowly to the reaction mixture comprising the polyunsaturated compound and the catalyst of the invention. An effective rate of addition is that which minimizes both the reaction exotherm and the extent of bis-hydrosilylation.

In another embodiment, the present invention is directed to the composition produced from the selective mono-hydrosilylation process described above. In the composition, the ratio of the mono-hydrosilylated product to the bis-hydrosilylated product is greater than about 1.8, specifically greater than about 3, more specifically greater than about 4.

Another preferred embodiment is the composition produced by the hydrosilylation of trivinylcyclohexane. The composition contains a monosilylated divinylcyclohexane product having one of the following general formulae:

(H₂C=CH)₂C₆H₉CH₂CH₂—Si(OR)₃     FORMULA XII (H₂C=CH)₂C₆H₉CH₂CH₂—SiR₃     FORMULA XIII (H₂C=CH)₂C₆H₉CH₂CH₂—Y     FORMULA XIV

In Formulae XII and XIII, R represents branched or straight-chained C1-C20 alkyl, C3-C20 cycloaliphatic or aromatic groups. The groups are not necessarily all the same in a single molecule. Thus, in Formula XIII, one R group can be octyl, another methyl and the third tert-butyl. R is methyl, ethyl or isopropyl in the preferred compounds of Formula XII and Formula XIII.

In Formula XIV, Y is a univalent siloxanyl radical of general formula (XV), (XVI) or (XVII) in which R represents branched or straight-chained C1-C20 alkyl, C3-C20 cycloaliphatic or aromatic groups, and x is greater than or equal to zero.

FORMULA XV:

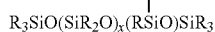

FORMULA XVI:

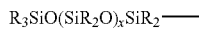

FORMULA XVII:

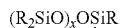

Examples of mono-hydrosilylated compounds of Formula XIV are

Commercial trivinylcyclohexane occurs primarily as mixtures of stereoisomers with vinyl groups at the 1, 2 and 4 positions. However, stereoisomers with 1,2,3- and 1,3,5-vinyl substitution are also known. The following specifications are based on the 1,2,4-isomeric mixture, but they are also generally applicable to the other two trisubstituted isomeric mixtures.

In the 1,2,4-trivinylcyclohexane stereoisomers, the differences are in the orientation of the vinyl groups relative to each other (cis versus trans), and relative to the cyclohexane ring (equatorial versus axial). This results in a total of eight stereoisomers, which occur as four mirror-image pairs of enantiomers. These four pairs, each being diastereomers of each other, can be separated from each other in the mixture by careful distillation. No separation by distillation occurs between the enantiomers of each pair. Thus, four compositions can be obtained, each being a racemic mixture of two mirror-image enantiomers. These four compositions will be referred to herein as Isomer A, Isomer B, Isomer C, and Isomer D, respectively. Their designations as A, B, C, or D are based on the order in which they are collected using a multi-plate distillation column, A being the first, and D the last.

Despite the ability to separate Isomers A, B, C, and D in principle, this is not trivial in practice. The boiling points of all four fall within a very narrow temperature range: about 3° C. or less. Moreover, two pairs, Isomers A and B, and Isomers C and D, boil within well under 1° C. of each other. Separating even just two components within this narrow boiling range requires good columns and tight process control. The occurrence of not two, but four components makes the separations substantially more challenging. Additional complications arise because the available commercial trivinylcyclohexane mixtures further contain a plethora of other impurities, the vast majority of them having boiling points close to that of the trivinylcyclohexane. The impurities consist of both lower boilers than trivinylcyclohexane and higher boilers.

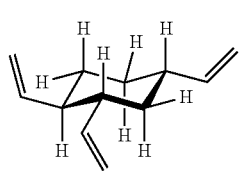

A

-continued

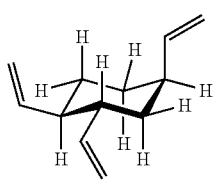
B

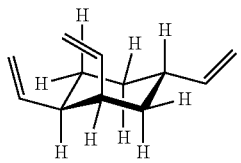
C

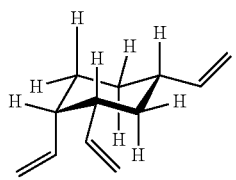
D

Four Isomeric Forms (A, B, C & D) of
1,2,4-Trivinylcyclohexane

Two-dimensional NMR correlation spectroscopy (COSY) has been used to assign the orientation of the vinyl groups in the Isomer A, B, C and D distillation fractions. The vinyl groups in Isomer A are all equatorial, while in Isomer B, only those at positions 1 and 2 are equatorial, and that at position 4 is axial. In Isomer C, the vinyl group at position 2 is axial and those at positions 1 and 4 are equatorial. In Isomer D, the axial vinyl group is at position 1; the equatorial vinyl groups are positions 2 and 4. The structures of Isomers A, B, C and D are shown above. These different structures determine the reactivity of the trivinylcyclohexane stereoisomers and the selectivity to mono-hydrosilylation products.

When hydrosilylation of the undistilled mixture of trivinylcyclohexane stereoisomers, or of the individual distillation fractions labeled Isomer A and B is catalyzed with the catalysts of the invention, for example iron pyridineimine catalysts, the initial addition of the silyl group occurs preferentially at the 4 position of the cyclohexane ring. This preference is significantly higher for the stereoisomers in the A fraction. Accordingly, not only is selective mono-hydrosilylation realized, but also regioselective mono-hydrosilylation at the 4 position. In contrast, platinum-catalyzed hydrosilylation of trivinylcyclohexane results in random addition of the silyl functionality to the vinyl groups with no particular preference for the 1, 2 or 4 position.

The catalyst precursor of the present invention, for example, the complex of Formula (I), after being activated in situ, allows the selective synthesis of 1,2-divinyl, 4-(2-triethoxysilylethyl)cyclohexane in at least 65 weight percent yield, preferably in at least 75 weight percent yield, from Isomer A and triethoxysilane. The gravimetric ratio of mono-hydrosilylated product to the bis-hydrosilylated product is greater than 2, preferably greater than 4 and most preferably greater than 6. 1,2-divinyl, 4-(2-triethoxysilylethyl)cyclohexane is a key intermediate in the synthesis of sulfur silanes useful for improving rolling resistance and wear in automobile tires. Accordingly, the present invention provides a useful way to selectively prepare this important intermediate.

Likewise, 1,2-divinyl, 4-(2-heptamethyltrisiloxanyl)cyclohexane, useful for forming homo and copolymer films, is obtained regioselectively from the reaction of Isomer A and/or Isomer B with bis(trimethylsiloxy)methylsilane catalyzed by in-situ activated catalyst precursor, for example iron pyridinediimine complexes of Formula (I). The gravimetric ratio of mono-hydrosilylated product to the bis-hydrosilylated product is greater than 3, preferably greater than 4 and most preferably greater than 6.

The catalyst precursors of the present invention, after being activated in situ, direct mono-hydrosilylation of Isomer C to either of the equatorial vinyl groups at positions 1 and 4 of the cyclohexane ring. Bis-hydrosilylation also occurs almost exclusively at these two positions. Thus, with Isomer C, regioselective bis-hydrosilylation is realized. Isomer D also shows a preference for regioselective bis-hydrosilylation. However, the addition occurs at the vinyl groups attached to positions 2 and 4 of the cyclohexane ring.

Accordingly, in one embodiment, the present invention relates to a process for selectively producing a mono-hydrosilylated product from a reaction mixture containing a silyl hydride and 1,2,4-trivinylcyclohexane comprising: (i) providing a catalyst precursor being a complex having a structural formula according to Formula (I), Formula (II) or Formula (III), (ii) activating the catalyst precursor by contacting the catalyst precursor with an activator in the presence of a liquid medium containing at least one component selected from the group consisting of a solvent, the silyl hydride, the 1,2,4-trivinylcyclohexane, and combinations thereof, thereby providing an activated catalyst; (iii) reacting the silyl hydride and the 1,2,4-trivinylcyclohexane in the presence of the activated catalyst such that hydrosilylation occurs selectively at the 4 position of the 1,2,4-trivinylcyclohexane, thereby producing the mono-hydrosilylated product, wherein step (ii) is conducted shortly before, or at the same time as, step (iii). The molar ratio of the Si—H functional groups in the silyl hydride to the alkenyl functional groups in the trivinylcyclohexane is between about (0.5:3) and about (1.1:3); and wherein the silyl group from the silyl hydride is selectively added to the 4 position of 1,2,4-trivinylcyclohexane.

In connection with the process, the silyl hydride can be triethoxysilane or bis(trimethylsiloxy)methylsilane. The trivinylcyclohexane can be a mixture of trivinylcyclohexane stereoisomers or trivinylcyclohexane isomer A and/or trivinylcyclohexane isomer B.

In addition to being effective in catalyzing selective mono-hydrosilylation reactions, the catalyst precursors of the present invention, upon activation, are also effective in catalyzing selective bis-hydrosilylation reactions. In some embodiments, the present invention provides a process for selectively producing bis-hydrosilylated reaction product from a composition containing a silyl hydride and a compound containing at least three unsaturated groups.

Illustratively, for Isomer C of 1,2,4-trivinylcyclohexane, mono-hydrosilylation occurs at either of the equatorial vinyl groups at positions 1 and 4 of the cyclohexane ring. The bis-hydrosilylation occurs almost exclusively at 1 and 4 positions of the cyclohexane ring. Thus, with Isomer C, regioselective bis-hydrosilylation is realized. Isomer D of 1,2,4-trivinylcyclohexane also shows a preference for regioselective bis-hydrosilylation. For Isomer D, the addition occurs at the vinyl groups attached to positions 2 and 4 of the cyclohexane ring.

The following examples are intended to illustrate, but in no way limit the scope of the present invention. All parts and percentages are by weight and all temperatures are in degrees Celsius unless explicitly stated otherwise.

EXAMPLES

The following abbreviations and terms are used:
bs—broad singlet
s—singlet
t—triplet
bm—broad multiple
GC—Gas Chromatography
MS—Mass Spectroscopy
THF—tetrahydrofuran

Example 1

Hydrosilylation of 1-Octene with Methylbis(trimethylsilyloxy)silane ($MD^HM$) with $NaEt_3BH$ as an activator and $^{2,6-Et2}PDIFeBr_2$ as a catalyst precursor ($^{2,6-Et2}PDI$)$FeX_2$ (X=Cl, Br), which structure is shown below, was synthesized according to: Schmidt, R.; Welch, M. B.; Palackal, S. J.; Alt, H. G. *Journal of Molecular Catalysis A: Chemical* (2002), 179(1-2), 155-173.

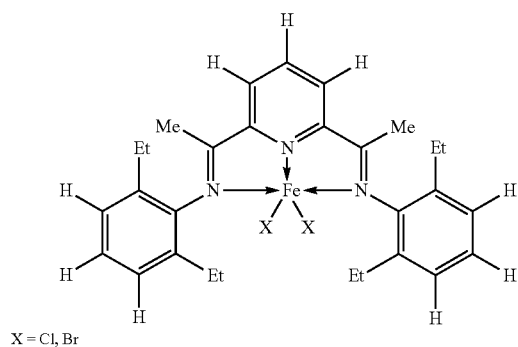

X = Cl, Br

In an inert atmosphere, to a scintillation vial was added 0.150 g (1.33 mmol) of 1-octene and 0.229 g (1.03 mmol) of $MD^HM$, followed by 0.006 g (0.01 mmol) of $^{2,6-Et2}PDIFeBr_2$ (1 mol % to silane). A stir bar was added and a blue slurry was formed. With stirring, 0.020 mL (0.02 mmol) of a 1M $NaEt_3BH$ solution in toluene was added. The reaction was stirred at room temperature (23° C.) for one hour, then the reaction was quenched in air and analyzed by GC and NMR. The resonance associated with the Si—H in the $^1$H NMR was observed to completely disappear, and a new resonance upfield at 0.41 ppm assignable to methylene attached to silicon appeared, giving a spectrum consistent with that of the previously reported compound (Poyatos, M.; Maisse-Francois, A.; Bellemin-Laponnaz, S.; Gade, L. H. Coordination chemistry of a modular N,C-chelating oxazole-carbene ligand and its applications in hydrosilylation catalysis. *Organometallics* (2006), 25(10), 2634-2641). No evidence was seen for any isomerization of the 1-octene or any hydrosilylation products derived therefrom.

Example 2

Hydrosilylation of allyl polyether having nominal structure $H_2C=CHCH_2O(C_2H_4O)_{8.9}CH_3$ with Methylbis(trimethylsilyloxy)silane ($MD^HM$) with $NaEt_3BH$ as an activator and $^{2,6-Et2}PDIFeBr_2$ as a catalyst precursor In an inert atmosphere, to a scintillation vial was added 1.000 g (2.11 mmol) of allyl polyether having nominal structure $H_2C=CHCH_2O(C_2H_4O)_{8.9}CH_3$ and 0.470 g (2.11 mmol) of $MD^HM$ to form a substrate solution. To a separate vial, 0.013 g (0.02 mmol) of $^{2,6-Et2}PDIFeBr_2$ (1 mol % to silane) was added to about 1.5 mL of THF to form a catalyst precursor solution. A stir bar was added to the catalyst precursor solution and a blue slurry was formed, and with stirring 0.040 mL (0.04 mmol) of a 1M $NaEt_3BH$ solution in toluene was added, immediately forming a red solution. The red iron solution was added to the stirring substrate solution, and the reaction was sealed and moved onto a 60° C. oil bath for 60 minutes. The product was analyzed by NMR-spectroscopy. The resonance associated with the Si—H in the $^1$H NMR completely disappeared, and a new resonance upfield at 0.43 ppm assignable to the methylene attached to silicon appeared, consistent with the formation of the desired anti-Markovnikov addition product. No evidence was seen for any isomerization of the allyl polyether or any hydrosilylation products derived there from.

Example 3

Hydrosilylation of 1-Octene with Methylbis(trimethylsilyloxy)silane ($MD^HM$) with $NaEt_3BH$ as an activator and [2,6-Diisopropyl-N-{(E)-1-[6-{[(1R)-1-1-tert-butyl ethyl]ethanimidoyl}-2-pyridinyl]ethylidene}aniline]iron dibromide as a catalyst precursor A. Preparation of catalyst precursor [2,6-Diisopropyl-N-{(E)-1-[6-{[(1R)-1-1-tert-butyl ethyl]ethanimidoyl}-2-pyridinyl]ethylidene}aniline]iron dibromide (A1) Preparation of 1-{6-[(2,6-Diisopropyl)ethanimidoyl]-2-pyridinyl}-1-ethanone A 250 mL round bottom flask was charged with 5.00 g (30.64 mmol) of 2,6-diacetylpyridine, 6.00 g (33.84 mmol) of 2,6-diisopropylaniline, and 100 mL of methanol. A catalytic amount of p-toluenesulfonic acid was added and the reaction mixture was refluxed overnight. The reaction mixture was then cooled to approximately 35° C. to 40° C. and filtered to remove 2,6-bis[1-(2,6-diisopropylphenylimino)ethyl]pyridine. The reaction solution was then placed at 0° C. for 24 hours, and the solid was filtered, yielding 4.25 g (43%) of the desired product as a yellow powder. $^1$H NMR (benzene-$d_6$, 20° C.): δ=1.21-1.14 (2 d, 12H, $CH_2CH_3$), 2.19 (s, 3H, $CH_3$), 2.52 (s, 3H, $CH_3$), 2.88 (sep, 2H, $CH_2CH_3$), 7.05-7.13 (m, 3H, Ar) and $CH_2CH_3$), 7.21 (t, 1H, p-py), 7.94 (d, 1H, py), 8.45 (d, 1H, py).

(A2) Preparation of 2,6-Diisopropyl-N-[(E)-1-(6-{[(1R)-1-1-tert-butyl ethyl]ethanimidoyl}-2pyridinyl)ethylidene]aniline A round bottom flask was charged with 3.10 grams (9.61 mmol) of 1-{6-[(2,6-diisopropylphenyl)ethanimidoyl]-2-pyridinyl}-1-ethanone, 1.5 g of (R)-(−)-2-amino-3-methylbutane (1.5 eq.), 100 mL of methanol, and a catalytic amount of p-toluenesulfonic acid. The solution was refluxed overnight into a Dean-Stark trap containing sodium sulfate and then cooled to 0° C. and filtered. The white powder was washed with cold methanol and dried on a high vacuum line overnight yielding 2.95 g (76%) of the desired compound. $^1$H NMR (benzene-$d_6$, 20° C.): δ=0.96 (s, 9H, $^tBu$), 1.08-1.16 (2 dd, 12H, $CH_2CH_3$), 2.20 (s, 3H, $CH_3$), 2.25 (s, 3H, $CH_3$), 2.88 (2 sep, 2H, $CH_2CH_3$), 2.94 (s, 3H, $^tBuCHCH_3$), 3.30 (q, 1H, 'Bu—CH—CH₃), 7.11-7.16 (m, 3H, Ar), 7.21 (t, 1H, p-py), 8.28 (d, 1H, py), 8.39 (d, 1H, py).

(A3) Preparation of [2,6-Diisopropyl-N-{(E)-1-[6-{[(1R)-1-1-tert-butyl ethyl]ethanimidoyl}-2-pyridinyl] ethylidene}aniline]iron dibromide In an inert atmosphere, a round bottom flask was charged with 2.5 g (6.61 mmol) of 2,6-diisopropyl-N-{(E)-1-[6-{[(1R)-1-1-tert-butyl ethyl]ethanimidoyl}-2-pyridinyl]ethylidene}aniline, 1.33 g (6.60 mmol) of FeBr₂ and 50 mL of THF. The reaction was stirred for twelve hours, at which time an equal volume of pentane was added resulting in the precipitation of the desired product which was collected on a sintered glass frit and dried under reduced pressure to yield 3.6 g (94%) of a blue paramagnetic powder. ¹H NMR (CD₂Cl₂, 20° C.): δ=−19.43, −15.21, −11.97, −7.08, −4.52, −2.59, −1.40, 5.47, 14.51, 16.52, 23.15, 44.85, 70.32, 83.38, 187.03.

The structure of the catalyst precursor is shown below:

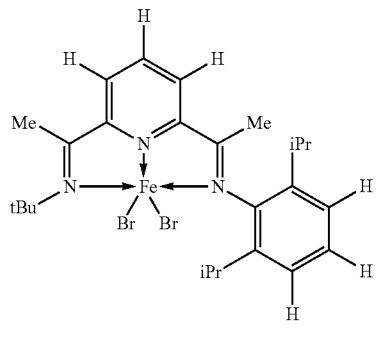

B. Hydrosilylation Reaction

A procedure similar to that in Example 1 was used, but with 0.150 g (1.33 mmol) of 1-octene and 0.229 g (1.03 mmol) of MD$^H$M, followed by 0.006 g (0.01 mmol) of [2,6-Diisopropyl-N-{(E)-1-[6-{[(1R)-1-1-tert-butyl ethyl]ethanimidoyl}-2-pyridinyl]ethylidene}aniline]iron dibromide (1 mol % to silane) and 0.020 mL (0.02 mmol) of a 1M NaEt₃BH solution. The reaction was stirred for 1 hour, after which the reaction was quenched in air and analyzed by GC, showing 30% conversion to the desired hydrosilylation product. Only the desired anti-Markovnikov addition product and unreacted starting materials were observed. No evidence was seen for any isomerization of the 1-octene or any hydrosilylation products derived there from.

Example 4

Hydrosilylation of 1-Octene with Methylbis(trimethylsilyloxy)silane (MD$^H$M) with Mg(butadiene).2THF as an activator and [2,6-Diisopropylphenyl-N-{(E)-1-[6-{[(1R)-1-1-tert-butyl ethyl]ethanimidoyl}-2-pyridinyl]ethylidene}aniline]iron dibromide as a catalyst precursor A procedure similar to that in Example 1 was used, but with 0.150 g (1.33 mmol) of 1-octene and 0.229 g (1.03 mmol) of MD$^H$M, followed by 0.006 g (0.01 mmol) of [2,6-Diisopropylphenyl-N-{(E)-1-[6-{[(1R)-1-1-tert-butyl ethyl]ethanimidoyl}-2-pyridinyl]ethylidene}aniline]iron dibromide (1 mol % to silane) and 0.003 g (0.014 mmol) of Mg(butadiene).2THF. The reaction was stirred for 1 hour, after which the reaction was quenched in air and analyzed by GC, showing 30% conversion to the desired hydrosilylation product. Only the desired anti-Markovnikov addition product and unreacted starting materials were observed. No evidence was seen for any isomerization of the 1-octene or any hydrosilylation products derived there from.

Example 5

Hydrosilylation of 1-Octene with Methylbis(trimethylsilyloxy)silane (MD$^H$M) with NaEt₃BH as an activator and $^{Cy}$APDIFeCl₂ ([2,6-Bis(N-cyclohexylacetimidoyl)pyridine]iron dichloride) as a catalyst precursor A. The Preparation of the Catalyst Precursor ($^{Cy}$APDI)FeCl₂ ([2,6-Bis(N-cyclohexylacetimidoyl)pyridine]iron dichloride), which structure is shown below, was synthesized according to: Castro, P. M.; Lappalainen, K.; Ahlgren, M.; Leskela, M.; Repo, T. *Journal of Polymer Science, Part A: Polymer Chemistry* (2003), 41(9), 1380-1389.

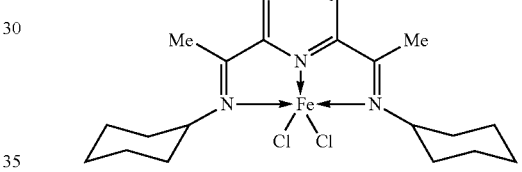

B. Hydrosilylation Reaction

A procedure similar to that in Example 1 was used, but with 0.100 g (0.89 mmol) of 1-octene and 0.192 g (0.86 mmol, 0.97 eq to olefin) of MD$^H$M, followed by 0.004 mg (0.01 mmol) of [2,6-Bis(N-cyclohexylacetimidoyl)pyridine]iron dichloride (1 mol % to silane) and 0.02 mL (0.02 mmol) of a 1M NaEt₃BH solution. The reaction was stirred for one hour, after which the reaction was quenched in air and analyzed by GC, showing 45% conversion to the desired hydrosilylation product. Only the desired anti-Markovnikov addition product and unreacted starting materials were observed. No evidence was seen for any isomerization of the 1-octene or any hydrosilylation products derived there from.

Example 6

Hydrosilylation of 1-Octene with Methylbis(trimethylsilyloxy)silane (MD$^H$M) with Mg(butadiene).2THF as an activator and $^{Cy}$APDIFeCl₂ ([2,6-Bis(N-cyclohexylacetimidoyl)pyridine]iron dichloride) as a catalyst precursor A procedure similar to that in Example 1 was used, but with 0.100 g (0.89 mmol) of 1-octene and 0.192 g (0.86 mmol, 0.97 eq to olefin) of MD$^H$M, followed by 0.004 mg (0.01 mmol) of [2,6-Bis(N-cyclohexylacetimidoyl)pyridine]iron dichloride (1 mol % to silane) and 0.003 g (0.015 mmol) of Mg(butadiene).2THF. The reaction was stirred for 1 hour, after which the reaction was quenched in air and analyzed by GC, showing 40% conversion to the desired hydrosilylation product. Only the desired anti-Markovnikov addition product and unreacted starting materials were observed. No evidence was seen for any isomerization of the 1-octene or any hydrosilylation products derived there from.

Example 7

Hydrosilylation of 1-Octene with Methylbis(trimethylsilyloxy)silane ($MD^HM$) with $NaEt_3BH$ as an activator and (2,2':6',2''-Terpyridine)$FeCl_2$ as a catalyst precursor (2,2':6',2''-Terpyridine)$FeCl_2$, which structure is shown below, was synthesized according to: Reiff, W. M.; Erickson, N. E.; Baker, W. A., Jr. *Inorganic Chemistry* (1969), 8(9), 2019-21.

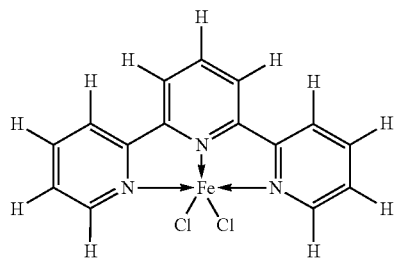

A procedure similar to that in Example 1 was used, but with 0.100 g (0.89 mmol) of 1-octene and 0.192 g (0.86 mmol, 0.97 eq to olefin) of $MD^HM$, followed by 0.004 mg (0.01 mmol) of (2,2':6',2''-terpyridine)iron dichloride (1 mol % to silane) and 0.02 mL (0.02 mmol) of a 1M $NaEt_3BH$ solution in toluene. The reaction was stirred for 1 hour, after which the reaction was quenched in air and analyzed by GC, showing 55% conversion to the desired hydrosilylation product. Only the desired anti-Markovnikov addition product and unreacted starting materials were observed. No evidence was seen for any isomerization of the 1-octene or any hydrosilylation products derived there from.

Example 8

Hydrosilylation of 1-Octene with Methylbis(trimethylsilyloxy)silane ($MD^HM$) with Mg(butadiene).2THF as an activator and (2,2':6',2''-Terpyridine)$FeCl_2$ as a catalyst precursor A procedure similar to that in Example 1 was used, but with 0.100 g (0.89 mmol) of 1-octene and 0.192 g (0.86 mmol, 0.97 eq to olefin) of $MD^HM$, followed by 0.004 mg (0.01 mmol) of (2,2':6',2''-terpyridine)iron dichloride (1 mol % to silane) and 0.003 g (0.015 mmol) of Mg(butadiene).2THF. The reaction was stirred for 1 hour, after which the reaction was quenched in air and analyzed by GC, showing 60% conversion to the desired hydrosilylation product. Only the desired anti-Markovnikov addition product and unreacted starting materials were observed. No evidence was seen for any isomerization of the 1-octene or any hydrosilylation products derived there from.

Example 9

Hydrosilylation of 1-Octene with Methylbis(trimethylsilyloxy)silane ($MD^HM$) with Mg(butadiene).2THF as an activator and ($^{2,6-Me2}$Quinoline)$FeCl_2$ as a precatalyst ($^{2,6-Me2}$Quinoline)$FeCl_2$, which structure is shown below, was synthesized according to: Zhang, S.; Sun, W.; Xiao, T.; Hao, X. *Organometallics* (2010), 29(5), 1168-1173.

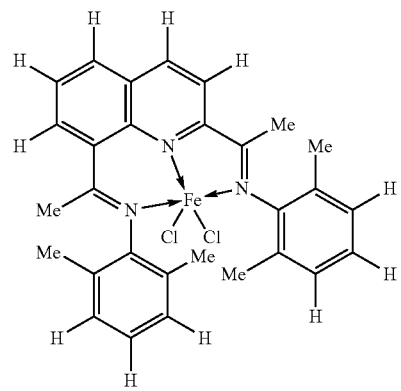

A procedure similar to that in Example 1 was used, but with 0.100 g (0.89 mmol) of 1-octene and 0.192 g (0.86 mmol, 0.97 equivalent to olefin) of $MD^HM$, followed by 0.004 mg (0.01 mmol) of [2,8-(2,6-Methyl$C_6H_3$N=CCH3)$_2C_9H_5$N] iron dichloride (1 mol % to silane) and 0.003 g (0.015 mmol) of Mg(butadiene).2THF. The reaction was stirred for 1 hour at room temperature (23° C.), after which the reaction was quenched in air and analyzed by GC, showing 70% conversion to the desired hydrosilylation product. Only the desired anti-Markovnikov addition product and unreacted starting materials were observed. No evidence was seen for any isomerization of the 1-octene or any hydrosilylation products derived there from.

Example 10

Hydrosilylation of 1-Octene with Methylbis(trimethylsilyloxy)silane ($MD^HM$) with $NaEt_3BH$ as an activator and $^{2,4,6-Me3}$PDIFeCl$_2$ as a catalyst precursor ($^{2,4,6-Me3}$PDI)$FeCl_2$, which structure is shown below, was synthesized according to Schmidt, R.; Welch, M. B.; Palackal, S. J.; Alt, H. G. *Journal of Molecular Catalysis A: Chemical* (2002), 179(1-2), 155-173.

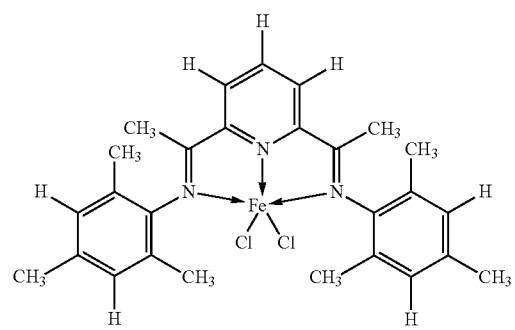

In an inert atmosphere, to a scintillation vial was added 0.100 g (0.891 mmol) of 1-octene and 0.200 g (0.892 mmol) of MD$^H$M, followed by 0.003 g (0.01 mmol) of $^{2,4,6-Me3}$PDIFeCl$_2$ (1 mol % to silane). A stir bar was added and a blue slurry was formed, and with stirring 0.020 mL (0.02 mmol) of a 1M NaEt$_3$BH solution in toluene was added. The reaction was stirred for 1 hour and the reaction was quenched in air and analyzed by GC and NMR. The resonance associated with the Si—H in the $^1$H NMR was observed to completely disappear during the course of the reaction, and a new resonance upfield at 0.41 ppm assignable to methylene attached to silicon appeared, giving a spectrum consistent with that of the previously reported compound. No evidence was seen for any isomerization of the 1-octene or any hydrosilylation products derived there from.

Example 11

Hydrosilylation of TVCH with Methylbis(trimethylsilyloxy)silane (MD$^H$M) with $^{2,4,6-Me3}$PDIFeCl$_2$ and NaEt$_3$BH as an activator In an inert atmosphere, to a scintillation vial was added 0.100 g (0.614 mmol) of 1,2,4-trivinylcyclohexane (predominantly isomer A) and 0.136 g (0.614 mmol) of MD$^H$M, followed by 0.003 g (0.01 mmol) of $^{2,4,6-Me3}$PDIFeCl$_2$ (1 mol % to silane). A stir bar was added and a blue slurry was formed, and with stirring 0.020 mL (0.02 mmol) of a 1M NaEt$_3$BH solution in toluene was added. The reaction was stirred for 1 hour and the reaction was quenched in air and analyzed by GC. The reaction mixture consisted of 72% of the monohydrosilylated product, predominantly at the C4 vinyl position.

Example 12

Crosslinking of M$^{vi}$D$_{120}$M$^{vi}$ and MD$_{15}$D$^H_{30}$M using $^{2,4,6-Me3}$PDIFeCl$_2$ with NaEt$_3$BH as an activator To a scintillation vial was added 1.0 g of M$^{vi}$D$_{120}$M$^{vi}$ and 44 mg of MD$_{15}$D$^H_{30}$M. Another vial was prepared containing 0.003 g of $^{2,4,6-Me3}$PDIFeCl$_2$ and 0.200 g of THF. 0.020 mL (0.02 mmol) of a 1M in toluene solution of NaEt$_3$BH was added to the iron solution, which was subsequently added to the stirring polymer solution. A crosslinked polymer was formed within seconds of the addition of the iron solution.

Example 13

Hydrosilylation of 1-Octene with Methylbis(trimethylsilyloxy)silane (MD$^H$M) with Diisobutylaluminum hydride (DIBALH) as an activator In an inert atmosphere, to a scintillation vial was added 0.100 g (0.891 mmol) of 1-octene and 0.200 g (0.892 mmol) of MD$^H$M, followed by 0.003 g (0.010 mmol) of $^{2,6-Me2}$PDIFeCl$_2$ (1 mol % to silane). A stir bar was added and a blue slurry was formed, and with stirring 0.020 mL (0.02 mmol) of a 1M DIBALH solution in toluene was added. The reaction was stirred for 1 hour and the reaction was quenched in air and analyzed by GC. The peak associated with the desired anti-Markovnikov product in the GC trace integrated to roughly 10% of the reaction mixture, which was comprised mainly of starting material and isomerized 1-octene.

While the above description contains may specifics, these specifics should not be constructed as limitations on the scope of the invention, but merely as exemplifications of preferred embodiments thereof. Those skilled in the art will envision many other possible variations that are within the scope and spirit of the invention as defined by the claimed appended hereto.

What is claimed is:

1. A process for the hydrosilylation of a reaction mixture containing a silyl hydride and a compound containing at least one unsaturated group, the process comprising:
   (i) providing a catalyst precursor being a complex having a structural formula according to Formula (I), Formula (II), or Formula (III);
   (ii) activating the catalyst precursor by contacting the catalyst precursor with an activator in the presence of a liquid medium containing at least one component selected from the group consisting of a solvent, the silyl hydride, the compound containing at least one unsaturated group, and combinations thereof, thereby providing an activated catalyst;
   (iii) reacting the silyl hydride, selected from the group consisting of R$_3$SiH, (RO)$_3$SiH, HSiR$_a$(OR)$_{3-a}$, R$_3$Si(CH$_2$)$_f$(SiR$_2$O)$_k$SiR$_2$H, (RO)$_3$Si(CH$_2$)$_f$(SiR$_2$O)$_k$SiR$_2$H, Q$_u$T$_v$T$^H_p$D$_w$D$^H_x$M$^H_y$M$_z$, and combinations thereof, wherein Q is SiO$_{4/2}$, T is R'SiO$_{3/2}$, T$^H$ is HSiO$_{3/2}$, D is R'$_2$SiO$_{2/2}$, D$^H$ is R'HSiO$_{2/2}$, M$^H$ is H$_g$R'$_{3-g}$SiO$_{1/2}$, M is R'$_3$SiO$_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of the all the elements in the silyl hydride are satisfied and the compound containing at least one unsaturated group in the presence of the activated catalyst to produce a hydrosilylation product containing the activated catalyst or derivatives thereof,
   wherein step (ii) is conducted shortly before, or at the same time as, step (iii); and
   (iv) optionally removing the activated catalyst or derivatives thereof,
   wherein Formula (I), Formula (II) and Formula (III) are:

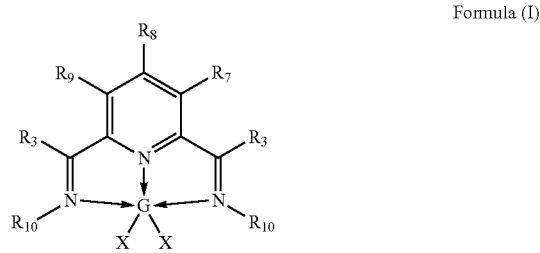

Formula (I)

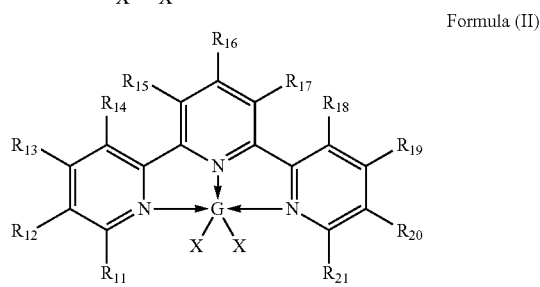

Formula (II)

-continued

Formula (III)

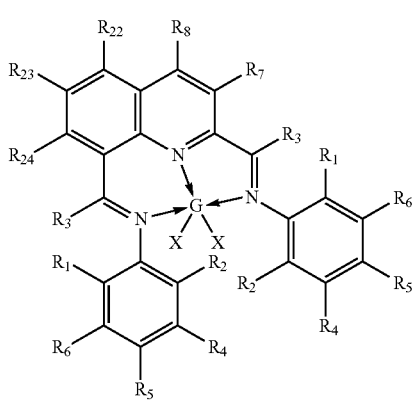

wherein
G is Mn, Fe, Ni, or Co;
each occurrence of $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ is independently H, C1-18 alkyl, C1-C18 substituted alkyl, aryl, substituted aryl, or an inert group, wherein any two of $R_1$-$R_3$, $R_3$-$R_7$, $R_3$-$R_9$, $R_{14}$-$R_{15}$ and $R_{17}$-$R_{18}$ vicinal to one another taken together may form a ring being a substituted or unsubstituted, saturated, or unsaturated cyclic structure, wherein $R_2$ to $R_9$, and $R_{11}$ to $R_{24}$ other than hydrogen, optionally contain at least one heteroatom;
each occurrence of $R_{10}$ is C1-C18 alkyl group or C1-C18 substituted alkyl, aryl or substituted aryl group, wherein $R_{10}$ optionally contains at least one heteroatom; and
X is an anion.

2. The process of claim 1 wherein the activator is a reducing agent having a reduction potential of >−0.6 v versus ferrocene in the presence of nitrogen.

3. The process of claim 2 wherein the reducing agent is selected from the group consisting of sodium naphthalenide, Mg(butadiene).2THF, NaEt$_3$BH, LiEt$_3$BH, Mg (Anthracenide).3THF, diisobutylaluminum hydride, and combinations thereof.

4. The process of claim 1 wherein X is F$^-$, Cl$^-$, Br$^-$, I$^-$, CF$_3$R$^{40}$SO$_3^-$ or R$^{50}$COO$^-$, wherein R$^{40}$ is a covalent bond or a C1-C6 alkyl group, and R$^{50}$ is a C1-C10 hydrocarbyl group.

5. The process of claim 1 wherein the complex according to Formula (I), Formula (II) or Formula (III) is immobilized on a support.

6. The process of claim 5 wherein the support is selected from the group consisting of carbon, silica, alumina, MgCl$_2$, zirconia, polyethylene, polypropylene, polystyrene, poly(aminostyrene), dendrimers, and combinations thereof.

7. The process of claim 5 wherein at least one of $R_1$ to $R_9$ or $R_{11}$ to $R_{24}$ contains a functional group that covalently bonds with the support.

8. The process of claim 1, wherein p, u, v, y, and z are from 0 to 10, w and x are from 0 to 100, wherein p+x+y equals 1 to 100.

9. The process of claim 1, wherein the compound containing an unsaturated group is selected from the group consisting of an alkyl-capped allyl polyether, a vinyl functionalized alkyl-capped allyl or methallyl polyether, a terminally unsaturated amine, an alkyne, a C2-C40 olefin, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

10. The process of claim 1, wherein the compound containing an unsaturated group is a polyoxyalkylene having the generic formula:

$$R^1(OCH_2CH_2)_z(OCH_2CHR^3)_w\text{—}OR^2 \quad \text{Formula (IV)},$$

$$R^2O(CHR^3CH_2O)_w(CH_2CH_2O)_z\text{—}CR^4_2\text{—}C\!\equiv\!C\text{—}CR^4_2\text{—}(OCH_2CH_2)_z(OCH_2CHR^3)_wR^5 \quad \text{Formula (V) or}$$

$$H_2C\!=\!CR^4CH_2O(CH_2OCH_2)_z(CH_2OCHR^3)_wCH_2CR^4\!=\!CH_2 \quad \text{Formula (VI)},$$

wherein each occurrence of R$^1$ is an unsaturated organic group containing from 2 to 10 carbon atoms, each occurrence of R$^2$ is independently hydrogen, vinyl, or a polyether capping group of from 1 to 8 carbon atoms, each occurrence of R$^3$ and R$^4$ are independently monovalent hydrocarbon groups, each occurrence of R$^5$ is vinyl, or a polyether capping group of from 1 to 8 carbon atoms, each occurrence of z is 0 to 100 inclusive, and each occurrence of w is 0 to 100 inclusive.

11. A process for selectively producing a mono-hydrosilylated product from a reaction mixture containing a silyl hydride and a polyunsaturated compound, the process comprising:

(i) providing a catalyst precursor being a complex having a structural formula according to Formula (I), Formula (II), or Formula (III);

(ii) activating the catalyst precursor by contacting the catalyst precursor with an activator in the presence of a liquid medium containing at least one component selected from the group consisting of a solvent, the silyl hydride, the polyunsaturated compound, and combinations thereof, thereby providing an activated catalyst;

(iii) reacting the silyl hydride, selected from the group consisting of R$_3$SiH, (RO)$_3$SiH, HSiR$_a$(OR)$_{3-a}$, R$_3$Si(CH$_2$)$_f$(SiR$_2$O)$_k$SiR$_2$H, (RO)$_3$Si(CH$_2$)$_f$(SiR$_2$O)$_k$SiR$_2$H, Q$_u$T$_v$T$_p^H$D$_w$D$^H_x$M$^H_y$M$_z$, and combinations thereof, wherein Q is SiO$_{4/2}$, T is R'SiO$_{3/2}$, T$^H$ is HSiO$_{3/2}$, D is R'$_2$SiO$_{2/2}$, D$^H$ is R'HSiO$_{2/2}$, M$^H$ is H$_g$R'$_{3-g}$SiO$_{1/2}$, M is R'$_3$SiO$_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of all the elements in the silyl hydride are satisfied and the polyunsaturated compound in the presence of the activated catalyst such that hydrosilylation occurs selectively at one unsaturated group of the polyunsaturated compound, thereby producing the mono-hydrosilylated product containing the activated catalyst or derivatives thereof;

wherein step (ii) is conducted shortly before, or at the same time as, step (iii); and (iv) optionally removing the activated catalyst or derivatives thereof, wherein Formula (I), Formula (II) and Formula (III) are:

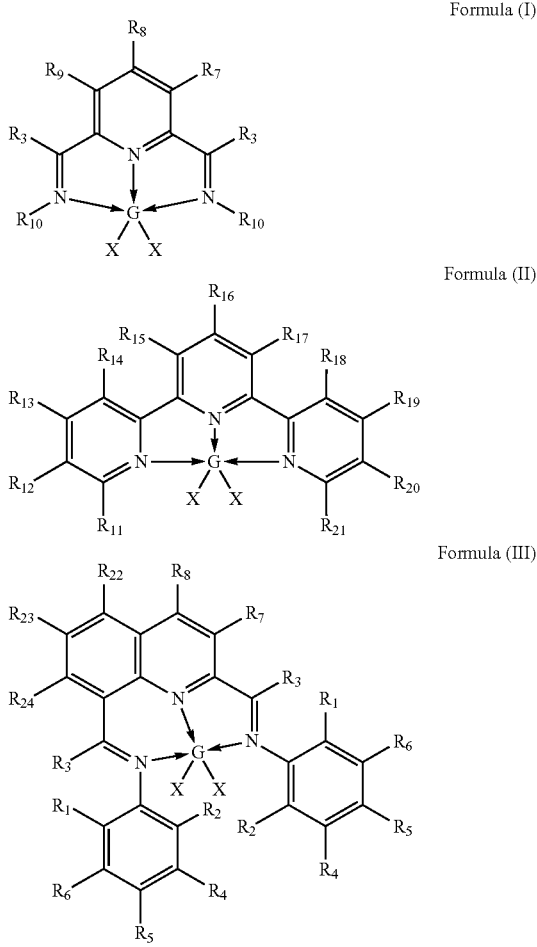

wherein
G is Mn, Fe, Ni, or Co;
each occurrence of $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ is independently H, C1-18 alkyl, C1-C18 substituted alkyl, aryl, substituted aryl, or an inert group, wherein any two of $R_1$-$R_3$, $R_3$-$R_7$, $R_3$-$R_9$, $R_{14}$-$R_{15}$ and $R_{17}$-$R_{18}$ vicinal to one another taken together may form a ring being a substituted or unsubstituted, saturated, or unsaturated cyclic structure, wherein $R_2$ to $R_9$, and $R_{11}$ to $R_{24}$ other than hydrogen, optionally contain at least one heteroatom;
each occurrence of $R_{10}$ is C1-C18 alkyl group or C1-C18 substituted alkyl, aryl or substituted aryl group, wherein $R_{10}$ optionally contains at least one heteroatom; and
X is an anion;
wherein the polyunsaturated compound is represented by Formula (X) or Formula (XI)

$E^1[(CH_2)_\beta CR^1=CH_2]_\alpha$, (Formula X)

$R^2_\gamma E^2[(CH_2)_\beta CR^1=CH_2]_\alpha$, (Formula XI)

wherein
$E^1$ is a divalent or polyvalent aliphatic or aromatic cyclic hydrocarbon group containing from 3 to 25 carbon atoms, or a divalent or polyvalent aliphatic or aromatic heterocyclic hydrocarbon containing from 3 to 25 carbon atoms, wherein the heteroatom is selected from the group consisting of oxygen, nitrogen, silicon and sulfur;
$E^2$ is a divalent or polyvalent cyclic silicone group containing from 3 to 8 silicon atoms and from 3 to 8 oxygen atoms;
each occurrence of $R^1$ and $R^2$ is independently a hydrogen or a hydrocarbon group containing from 1 to 8 carbon atoms;
each occurrence of $\alpha$, $\beta$ and $\gamma$ is independently an integer, wherein $\alpha$ is 2 to 6; $\beta$ is 0 to 6; and $\gamma$ is 0 to 4; and
wherein the molar ratio of the Si—H functional groups in the silyl hydride to the alkenyl functional groups in the unsaturated compound is between about $(0.5/\alpha)$ and about $(1.1/\alpha)$.

12. The process of claim 11 wherein the molar ratio of the Si—H functional groups in the silyl hydride to the alkenyl functional groups in the unsaturated compound is about $1/\alpha$.

13. The process of claim 11 wherein the unsaturated compound is selected from the group consisting of trivinylcyclohexanes, tetravinylcyclobutane, trivinyltrimethylcyclotrisiloxane, tetramethyltetravinylcyclotetrasiloxane, triallylcyanurate, and triallylisocyanurate.

14. The process of claim 11 wherein the unsaturated compound is trivinylcyclohexane.

15. The process of claim 11 wherein the silyl hydride has one of the following structures:

$R^3_a(R^4O)_b SiH$ (Formula XV)

(Formula VII)

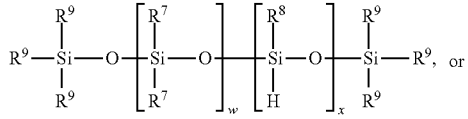

(Formula VIII)

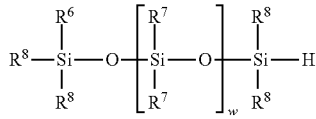

wherein each occurrence of $R^3$, $R^4$, $R^7$, $R^8$, and $R^9$ is independently a C1-$C_{1-8}$ alkyl, C1-C18 substituted alkyl, aryl, or substituted aryl, $R^6$ is hydrogen, a C1-C18 alkyl, C1-C18 substituted alkyl, aryl, or substituted aryl, x and w are independently greater than or equal to 0, a and b are integers from 0 to 3 provided that the a+b=3.

16. The process of claim 11 wherein the silyl hydride is selected from the group consisting of $(CH_3O)_3SiH$, $(C_2H_5O)_3SiH$, $(CH_3)_3SiOSi(CH_3)_2H$, $[(CH_3)_3SiO]_2SiH(CH_3)$, $[(CH_3)_2SiO]_3OSiH(CH_3)$ and $[(CH_3)_2SiO]_4OSiH(CH_3)$.

17. The process of claim 11 wherein the activator is a reducing agent having a reduction potential of $>-0.6$ v versus ferrocene in the presence of nitrogen.

18. The process of claim 17 wherein the reducing agent is selected from the group consisting of sodium naphthalenide, Mg(butadiene).2THF, NaEt$_3$BH, LiEt$_3$BH, Mg (Anthracenide).3THF, diisobutylaluminum hydride, and combinations thereof.

19. The process of claim 11 wherein X is $F^-$, $Cl^-$, $Br^-$, $I^-$, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group.

20. The process of claim 11 wherein the complex according to Formula (I), Formula (II) or Formula (III) is immobilized on a support.

21. A process for selectively producing a mono-hydrosilylated product from a reaction mixture containing a silyl hydride and 1,2,4-trivinylcyclohexane, the process comprising:

(i) providing a catalyst precursor being a complex having a structural formula according to Formula (I), Formula (II), or Formula (III);

(ii) activating the catalyst precursor by contacting the catalyst precursor with an activator in the presence of a liquid medium containing at least one component selected from the group consisting of a solvent, the silyl hydride, the 1,2,4-trivinylcyclohexane, and combinations thereof, thereby providing an activated catalyst;

(iii) reacting the silyl hydride, selected from the group consisting of $R_3SiH$, $(RO)_3SiH$, $HSiR_a(OR)_{3-a}$, $R_3Si(CH_2)_f(SiR_2O)_kSiR_2H$, $(RO)_3Si(CH_2)_f(SiR_2O)_kSiR_2H$, $Q_uT_vT_p^HD_wD^H_xD^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $H_gR'_{3-g}SiO_{1/2}$, M is $R'_3SiO_{1/2}$, each occurrence of R and R' is independently C1-C18 alkyl, C1-C18 substituted alkyl, aryl, or substituted aryl, wherein R and R' optionally contain at least one heteroatom, each occurrence of a independently has a value from 1 to 3, f has a value of 1 to 8, k has a value of 1 to 11, g has a value of from 1 to 3, p is from 0 to 20, u is from 0 to 20, v is from 0 to 20, w is from 0 to 1000, x is from 0 to 1000, y is from 0 to 20, and z is from 0 to 20, provided that p+x+y equals 1 to 3000, and the valences of all the elements in the silyl hydride are satisfied and the 1,2,4-trivinylcyclohexane in the presence of the activated catalyst such that hydrosilylation occurs selectively at the 4 position of the 1,2,4-trivinylcyclohexane, thereby producing the mono-hydrosilylated product, wherein step (ii) is conducted shortly before, or at the same time as, step (iii); and wherein Formula (I), Formula (II) and Formula (III) are:

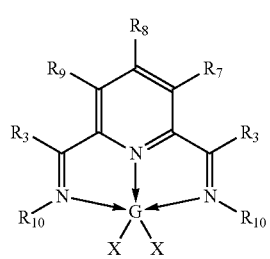

Formula (I)

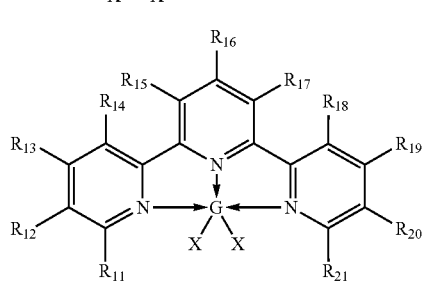

Formula (II)

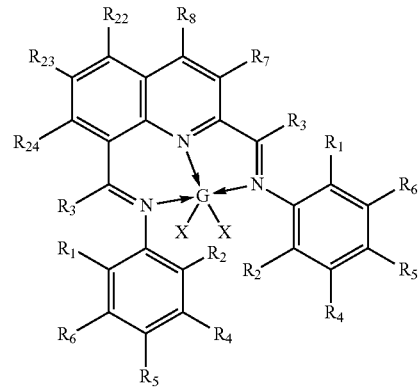

Formula (III)

wherein

G is Mn, Fe, Ni, or Co;

each occurrence of $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ is independently H, C1-18 alkyl, C1-C18 substituted alkyl, aryl, substituted aryl, or an inert group, wherein any two of $R_1$-$R_3$, $R_3$-$R_7$, $R_3$-$R_9$, $R_{14}$-$R_{15}$ and $R_{17}$-$R_{18}$ vicinal to one another taken together may form a ring being a substituted or unsubstituted, saturated, or unsaturated cyclic structure, wherein $R_2$ to $R_9$, and $R_{11}$ to $R_{24}$ other than hydrogen, optionally contain at least one heteroatom;

each occurrence of $R_{10}$ is C1-C18 alkyl group or C1-C18 substituted alkyl, aryl or substituted aryl group, wherein $R_{10}$ optionally contains at least one heteroatom; and X is an anion;

wherein the molar ratio of the Si—H functional groups in the silyl hydride to the alkenyl functional groups in the 1,2,4-trivinylcyclohexane is between about (0.5/3) and about (1.1/3).

22. The process of claim 21 wherein the silyl hydride is triethoxysilane.

23. The process of claim 21 wherein the silyl hydride is bis(trimethylsiloxy)methylsilane.

24. The process of claim 21 wherein the 1,2,4-trivinylcyclohexane is a mixture of 1,2,4-trivinylcyclohexane stereoisomers.

25. The process of claim 21 wherein the 1,2,4-trivinylcyclohexane is 1,2,4-trivinylcyclohexane isomer A and/or 1,2,4-trivinylcyclohexane isomer B, wherein isomer A and isomer B have structure Formulae (XIX) and (XX):

(Formula XIX)

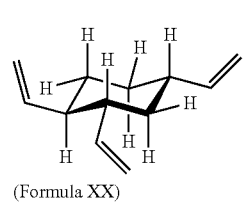

Isomer A (Formula XX)

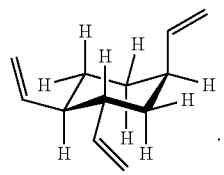
Isomer B
* * * * *